US008182747B2

(12) United States Patent
Marquant et al.

(10) Patent No.: US 8,182,747 B2
(45) Date of Patent: May 22, 2012

(54) TEST DEVICE FOR ANALYZING A BIOLOGICAL SAMPLE LIQUID

(75) Inventors: Michael Marquant, Mannheim (DE); Volker Unkrig, Ladenburg (DE); Fritz Hindelang, Carlsberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 969 days.

(21) Appl. No.: 10/628,042

(22) Filed: Jul. 25, 2003

(65) Prior Publication Data
US 2004/0154923 A1 Aug. 12, 2004

(30) Foreign Application Priority Data
Jul. 31, 2002 (DE) .................................. 102 34 819

(51) Int. Cl.
*G01N 27/26* (2006.01)
(52) U.S. Cl. .................. 422/82.02; 422/82.01; 422/502; 422/503
(58) Field of Classification Search ............... 422/82.01, 422/82.02, 82.03, 502, 503
See application file for complete search history.

(56) References Cited

U.S. PATENT DOCUMENTS

| | | | | |
|---|---|---|---|---|
| 4,118,305 A | * | 10/1978 | Oloman et al. ................ | 204/265 |
| 4,952,266 A | | 8/1990 | Tsuruta et al. | |
| 5,141,614 A | * | 8/1992 | Akridge et al. ........... | 204/192.15 |
| 5,376,252 A | * | 12/1994 | Ekstrom et al. ................ | 204/603 |
| 5,565,143 A | * | 10/1996 | Chan .............................. | 252/514 |
| 5,591,403 A | | 1/1997 | Gavin et al. ..................... | 422/73 |
| 5,681,529 A | | 10/1997 | Taguchi et al. | |
| 5,922,604 A | * | 7/1999 | Stapleton et al. ............... | 436/46 |
| 5,997,817 A | * | 12/1999 | Crismore et al. .......... | 204/403.1 |
| 6,060,323 A | | 5/2000 | Jina | |
| 6,167,910 B1 | * | 1/2001 | Chow ............................ | 137/827 |
| 6,482,306 B1 | * | 11/2002 | Yager et al. .................... | 204/600 |
| 6,521,182 B1 | | 2/2003 | Shartle et al. | |
| 7,005,109 B2 | | 2/2006 | Husar | |
| 2001/0027745 A1 | * | 10/2001 | Weigl et al. .................... | 117/206 |
| 2002/0053523 A1 | * | 5/2002 | Liamos et al. ................. | 205/787 |
| 2002/0061260 A1 | * | 5/2002 | Husar ........................... | 422/100 |
| 2002/0079219 A1 | * | 6/2002 | Zhao et al. ..................... | 204/451 |
| 2003/0141189 A1 | * | 7/2003 | Lee et al. ....................... | 204/600 |

FOREIGN PATENT DOCUMENTS

| | | |
|---|---|---|
| EP | 0021798 B1 | 1/1981 |
| EP | 0537761 B1 | 4/1993 |
| JP | 06308131 | 11/1994 |
| WO | WO 99/29429 | 6/1999 |
| WO | WO99/30152 A1 | 6/1999 |
| WO | WO 01/25137 A | 4/2001 |
| WO | WO 01/89695 A | 11/2001 |

* cited by examiner

*Primary Examiner* — In Suk Bullock
*Assistant Examiner* — Paul Hyun
(74) *Attorney, Agent, or Firm* — Barnes & Thornburg LLP

(57) ABSTRACT

The invention concerns a test device for analyzing especially a biological sample liquid comprising a composite body consisting of a plurality of layers of flat materials and a sample channel located in the composite body for transporting the sample liquid from an application site to a measuring site. According to the invention it is proposed that the composite body has a plurality of transport layers arranged in a stack-like manner between support layers for holding in each case sample channel.

18 Claims, 5 Drawing Sheets

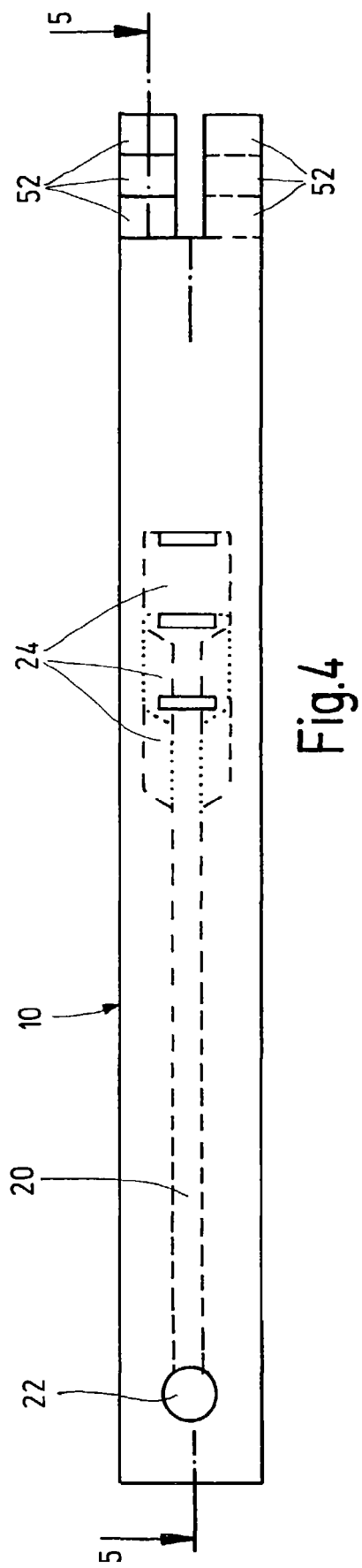
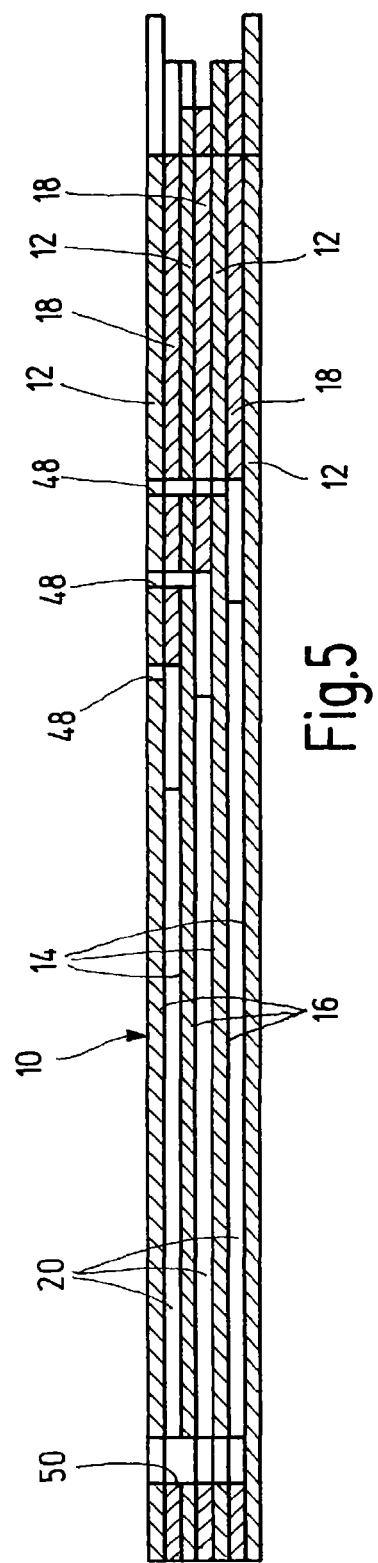
Fig.4
Fig.5

TEST DEVICE FOR ANALYZING A BIOLOGICAL SAMPLE LIQUID

BACKGROUND OF THE INVENTION

1. Field of the Invention

The invention concerns a test device for analysing in particular a biological sample liquid comprising a composite body formed from several layers of flat material and at least one sample channel located in the composite body for transporting the sample liquid from a site of application to a measuring site. The invention also concerns a process for producing such a test device and preferred uses thereof.

2. Description of Related Art

An analytical disposable test element for determining an analyte in a liquid is known from WO 99/29429 which enables a spatial separation between the sample application site and the detection zone while using minimal sample volumes. A single channel capable of capillary liquid transport is provided for this purpose and the geometry of this channel is determined by an intermediate layer while a support and a cover made of a flat material provide a lower and upper boundary. It is essential for such diagnostic systems that the accuracy of the results measured by the system is ensured at all times. Poor maintenance of instruments, incorrect storage of reagents, test strips or system fluids, exceeding expiry dates or incorrect handling by the user are only some of the reasons which can lead to incorrect measuring results in practice. Hence controls are commonly used for the quality control of test carriers in which liquid reagents are applied to the test strip instead of sample material in order to generate measuring results that are within the specified target ranges. A disadvantage of this method is that the checked test carrier is consumed by this process and is no longer available for measuring the actual sample material. Hence this method only allows a random check of samples taken from a large number of test carriers.

In order to overcome this disadvantage U.S. Pat. No. 5,591,403 discloses the provision of several sample channels located in one plane which are all filled with the same sample liquid where at least one channel contains a control substance. A disadvantage of such planar channel geometries is that they are complicated and costly to manufacture. In particular it is difficult to integrate different reagents in channels that are in close proximity while strictly separating the individual processes.

Hence the object of the invention was to avoid the disadvantages of the prior art described above and to achieve a design which is technically more advantageous to manufacture and is also more compact which can also be used to carry out more complex test formats. An additional aim is to describe a simple manufacturing process for such test devices and test elements.

SUMMARY OF THE INVENTION

The invention provides for a device for analyzing a biological liquid sample. The device includes a composite body of plurality of layers of flat material defining at least one sample channel for transporting the sample liquid from an application site to a measuring site wherein the plurality of layers of flat material comprise a plurality of transport layers arranged in a stack-like manner between support layers.

BRIEF DESCRIPTION OF THE FIGURES

FIG. 4 shows another embodiment of a test strip with air-bleed holes of the sample channels located on the broad side and contact tongues protruding from the end.

FIG. 5 shows a section along the step-shaped cutting line 5-5 of FIG. 4.

DETAILED DESCRIPTION

Figure 1:
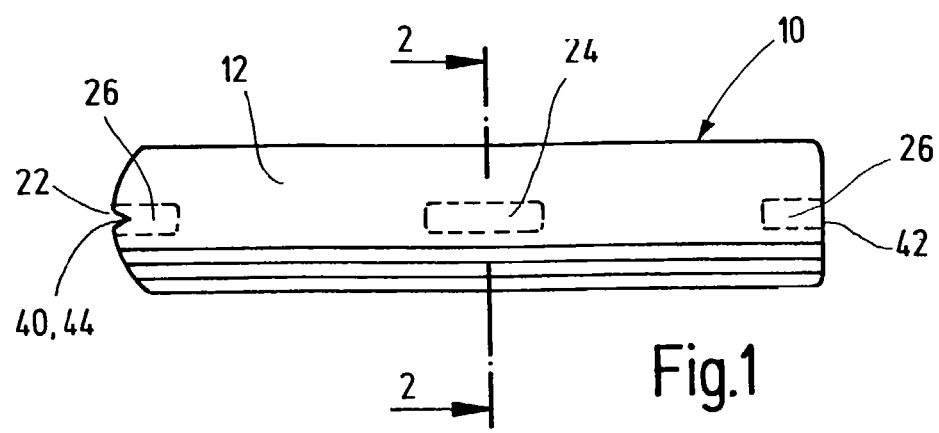
FIG. 1 shows a test device formed as a test strip from several stacked layers of flat material for the electrochemical analyses of a liquid sample such as blood.

The core of the invention is to provide a multi-test element in a stacked arrangement containing unbranched sample channels lying above one another. Correspondingly the invention proposes that the composite body has several transport layers in a stacked arrangement between support layers each of which is used to hold a sample channel leading to an associated measuring site. This allows a plurality of sample channels to be arranged above one another in a simple, multiply repeated layer structure in a compact structure that is simple to manufacture. This is also very advantageous for packaging and adaptation in a measuring instrument. Furthermore it is possible to prevent carry over of various reagents during the manufacture by the ability to chronologically and spatially separate their application on the various layers of material which are not assembled on top of one another until a later time.

The sample channels are preferably aligned on top of one another in the direction in which the transport layers are stacked in order to also further simplify the sample application. An advantageous embodiment provides that the sample channels are kept clear as a continuous free space between in each case two special sections of the transport layers and in particular are cut free by dividing or punching out the transport layers.

In order to simplify an arrangement of electrodes in the area of the sample channels, the transport layers should consists of an electrically insulating foil material. The electrodes can be advantageously made by placing a geometric structure or a complete coat of an electrode layer made of an electrically conductive material on the sides of the support layers that face the transport layers. Another advantageous embodiment provides that the opposing electrode layers on both sides of the transport layers form an electrode pair in the area of the measuring sites for the electrochemical analysis of a sample property. For this purpose it is advantageous when the opposing electrode layers are in pairs consisting of a noble metal, preferably gold, platinum or palladium as the measuring electrode and a silver-silver chloride mixture as a counter reference electrode.

The electrode layers can also be used as a signal pick-up in a detection instrument. Hence it is advantageous when the edges of the electrode layers have a connecting member extending beyond the adjacent transport layer as an electrical contact. A further improvement can be achieved when the support layers are displaced relative to one another in a step-like manner in an edge region.

Each of the transport layers is advantageously separated from at least one adjacent electrode layer by an electrically insulating foil mask where the foil mask has perforations in the area of the sample channel to form spatially defined measuring fields at the intended sites of measurement. In this connection a hydrophilic material at the same time ensures that they are also readily and rapidly filled with a water-based sample liquid.

For the actual detection of the analyte and for monitoring the test it is possible in a simple manner to apply reagents, preferably as a dry substance, which can be taken up by the sample liquid in the area of the measuring sites.

The sample channels are advantageously designed for the automatic capillary transport of sample liquid between the site of application and the respective measuring sites as capillary channels.

The compact arrangement enables several sample channels to be filled simultaneously by immersion in the liquid sample to be imbibed. Correspondingly an advantageous embodiment provides that the application site is formed by an edge zone of the composite body which encompasses the inlet openings of the sample channels and can be immersed in the sample liquid. Alternatively the application site can also be formed by a recess in the composite body which communicates with the sample channels and can be filled with an aliquot of the sample liquid.

In order to reliably prevent an intermixing of the sample liquid that may be loaded with various reagents in the outlet area of the sample channels, it is advantageous when the sample channels are connected to venting channels on the outer side of the composite body which run crosswise to the layers of flat material and are laterally spaced from one another.

In order to check the filling of the sample channels, suitable detection means for the sample liquid that flows through are provided at least one control site. This can be achieved in a particularly simple manner by measuring the change in the alternating current conductivity value during the sample application by means of electrodes that are present for the actual test.

A preferred embodiment for carrying out optical analyses provides that the support layers form a transparent measuring window at least in the area of the measuring sites.

It is advantageous for the manufacturing process when the composite body consists of strips of foil glued together in stacks.

A particularly preferred process for producing a test device according to the invention provides that the layers of flat material are transported from roll to roll as rolls of tape material and are glued together in a stack-like manner during their transport, are optionally provided with reagents and subsequently divided into test strips. This allows a continuous production process in a simple manner.

Another aspect of the invention relates to a preferred use of the multiple test devices according to the invention for determining different parameters in the sample liquid each in associated sample channels. Another particularly advantageous use is the simultaneous detection of measuring parameters of the sample liquid and of control parameters to check the validity or to calibrate the measuring parameters in the respective sample channels.

The invention is further elucidated in the following on the basis of the embodiments shown in a schematic manner in the Figures.

The test strips shown in the drawing are composite bodies 10 essentially consisting of several support layers 12 optionally provided with electrode layers 14, 16 and transport layers 18 arranged between them, each of which holds a sample channel 20 wherein a sample liquid that is to be analysed electrochemically or optically is transported via the capillary-active sample channels from an application site 22 to in each case at least one measuring zone or measuring site 24.

Figure 2:
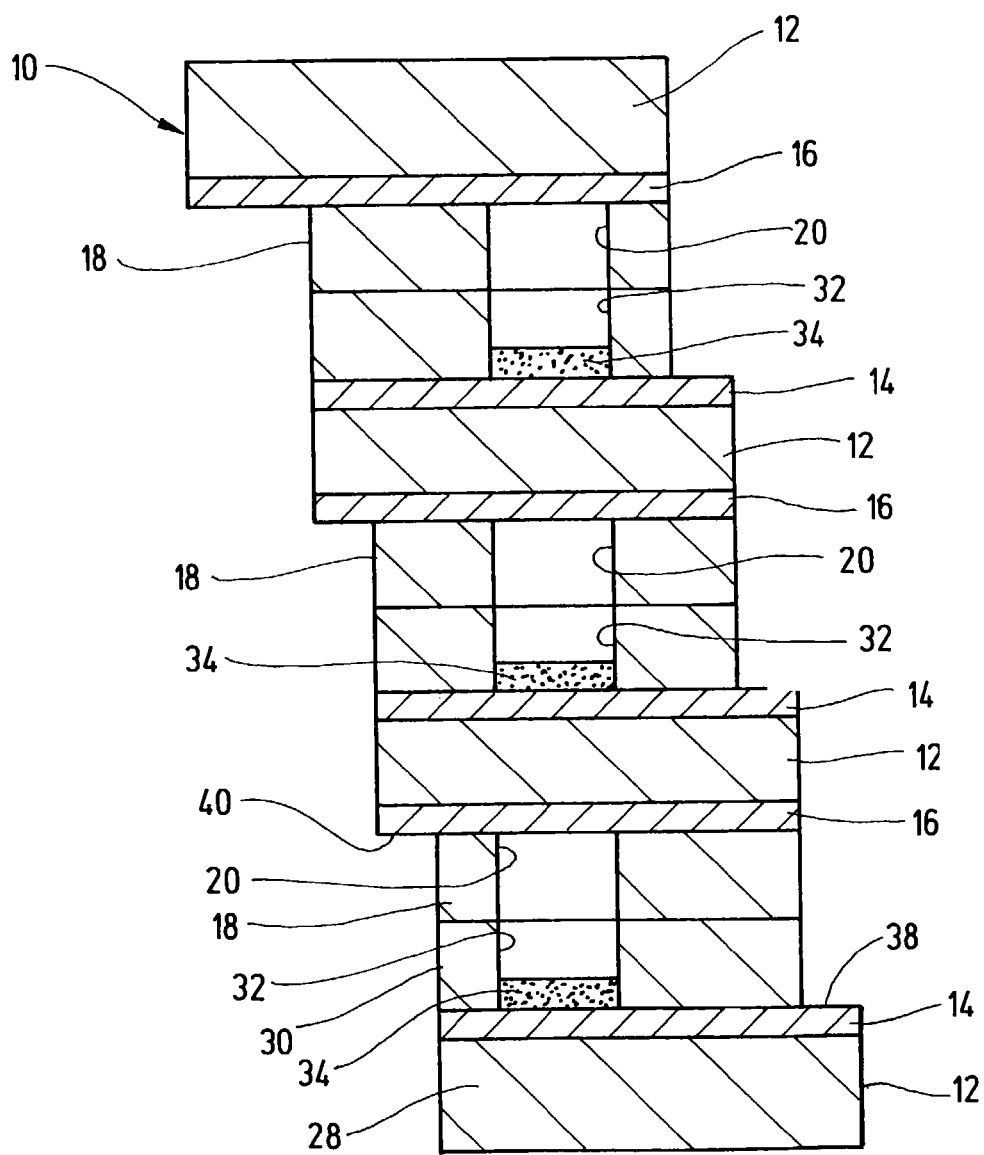
FIG. 2 shows a cross section along the cutting line 2-2 of FIG. 1 which is rotated into the vertical.

As shown in FIG. 2 the sample channels 20 each of which is individually kept clear in the stack of transport layers 18 are arranged above one another in the direction of the stack i.e. at right angles to the material layers to achieve a particularly advantageous design. This also enables unstructured electrode layers 14, 16 covering the whole area to be used on the support layers 12 covering the sample channels 20 and thus avoiding a branching channel geometry.

Figure 3:
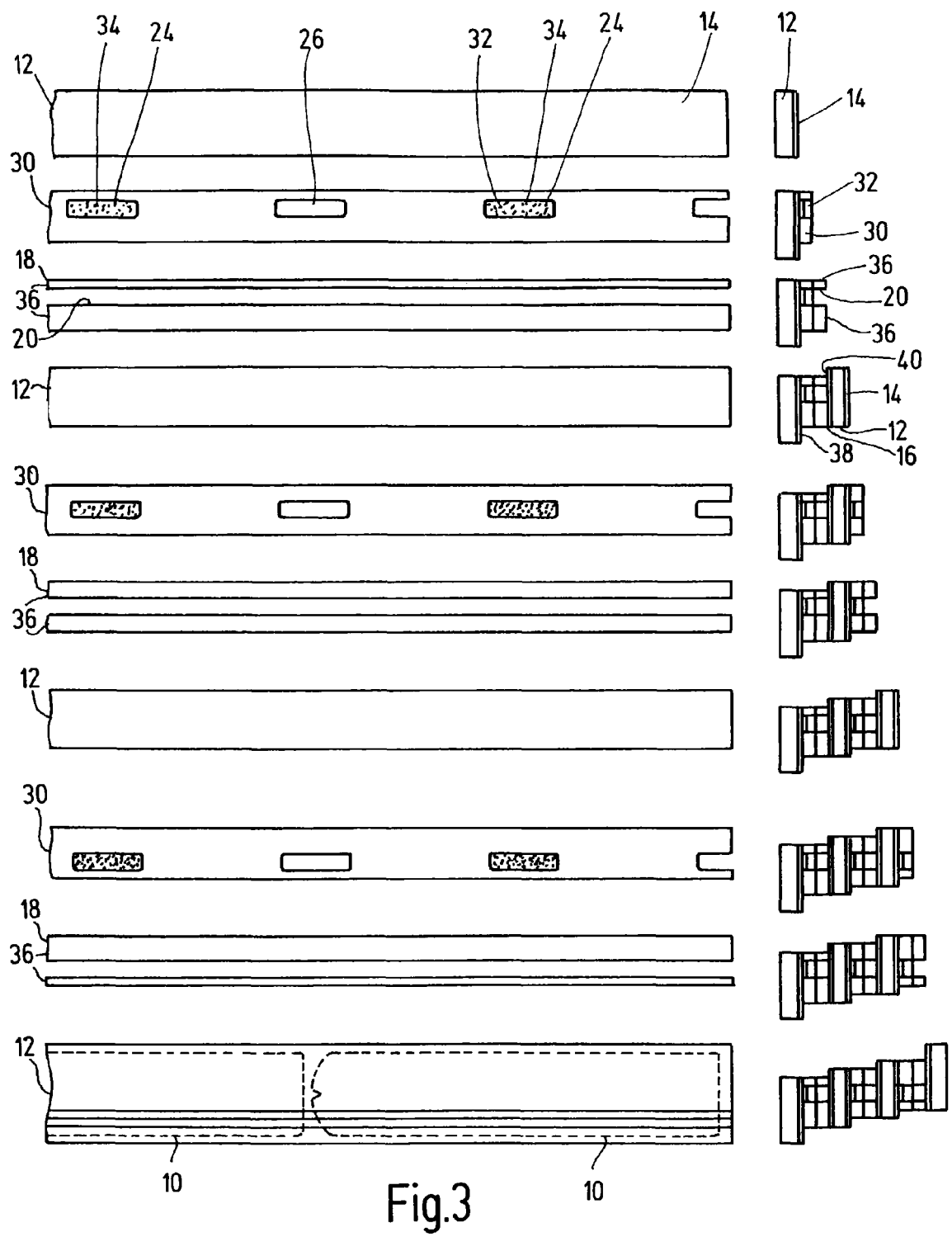
FIG. 3 shows the layered structure of the test strip in a top-view and end-view starting with the lower layer.

FIG. 3 shows the structure of the test strips 10 in more detail as sections of foil tapes that are glued together. A polyester foil 28 that is vapour-coated with a gold layer 14 as an electrode surface forms the lower support layer 12. An electrically insulating foil mask 30 is glued onto the gold layer 14 which also has permanent good wetting properties for the sample liquid. The foil mask 30 is provided with punched holes or perforations 32 in an area that borders the bottom of the sample channel at the central measuring site 24 and additionally at control sites 26 at the inlet and outlet as a result of which the electrode fields of the gold layer 14 are bounded at the corresponding sections of the sample channel 20. In order to electrochemically detect sample properties, reagents 34 that can be taken up by the inflowing sample liquid are dispensed or applied to the area of the gold layer 14 and then dried at the measuring site 24 in the corresponding perforation 32. The control sites 26 are used to check the filling of the sample channel 20 by measuring the electrical conductivity which is influenced by the flowing sample liquid.

Two double-sided adhesive tapes 36 are glued laterally spaced apart on the foil mask 30 as a first transport layer 18. The opposing longitudinal edges of the adhesive strips 36 thus form the lateral boundary for a continuous sample channel 20 which results in a capillary action for the automatic transport of sample liquid if the dimensions are appropriate. Another support layer 12 is applied over the first transport layer 18 formed in this manner, whose underside is coated with a silver-silver chloride mass as an electrode area 16 and whose upper side is vapour-coated or sputtered with gold. In this manner the electrode layers 14, 16 opposing each other on both sides of the first transport layer 18 form an active electrode pair in the area of the perforations 32 which consists of the gold layer 14 as the measuring electrode and the silver-silver chloride layer 16 as the counter reference electrode. In order to enable an electrical contact with the electrodes, the support layers 12 are laterally displaced in such a manner that connecting strips 38, 40 extending in the longitudinal direction protrude and are freely accessible.

The structure described above is duplicated according to FIG. 3 to finally form three similar sample channels 20 stacked on top of one another which, if necessary only differ by the incorporated reagent 34.

In order to simplify the production, the individual layers are firstly present as rolls of tape that are transported from roll to roll in an assembly device that is not shown and are glued together in a stack-like manner during their transport. The individual test strips 10 are then formed by punching out sections of the tape as shown in the lower part of FIG. 3 by the dashed contour. The cutting operation generates the inlet openings 40 of the sample channels at the application site 22 for filling and also forms the vent openings 42 at the other end of the strip (FIG. 1). In order to facilitate the aspiration of sample liquid, the inlet openings 40 are deepened by a notch 44 in the end of the test strip.

The embodiments of a test strip 10 shown in FIGS. 4 to 8 are provided with functionally the same parts with the same reference numerals as described above.

Figure 6:
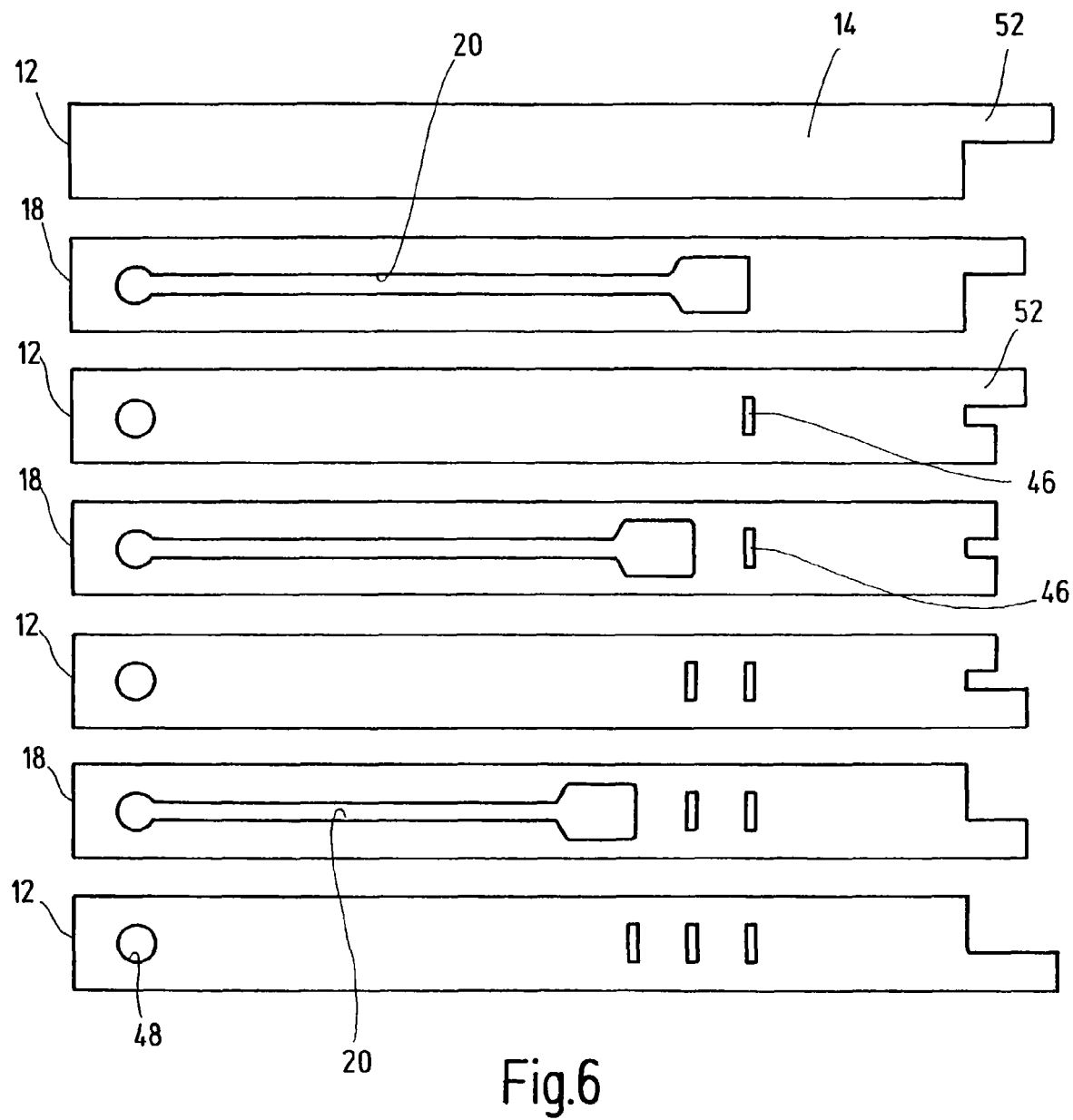
FIG. 6 shows the layered structure of the test strip of FIG. 5 in a top-view beginning with the lower layer.

The main difference between the embodiments of FIGS. 4 to 6 is that the free space in the support layers 18 for the sample channel 20 is punched out with a closed cutting line. Hence the strips are not assembled from the roll but rather by means of a stacked assembly of individually pre-punched layers. The measuring sites 24 are formed by end sections of the sample channels 20 which may be optionally widened and are displaced relative to one another in the longitudinal direction of the strip. This enables venting channels 48 to be produced in the individual layers by congruent perforations 46 which extend in the direction of the stack and end at the top side of the strip while being spaced apart in the longitudinal direction of the strip in order to reliably prevent intermixing of the sample liquid that is mixed with the dissolved reagents in the vicinity of the measuring sites 24.

A circular hole is punched out of all foil layers with the exception of the lowest support foil 12 in the area of the application site. This produces an inlet chamber 50 from which all three sample channels 20 originate and can be filled with sample liquid.

The electrical connections of the electrode layers 14, 16 are formed at the end of the strip by staggered protruding tongues 52 of the support layers 12.

In this embodiment it is also in principle possible to produce an electrode region whose area is delimited relative to the opposing counterelectrode layer 16 by means of additional hydrophilic masking foils which are directly glued onto the gold layer 14.

Figure 7:
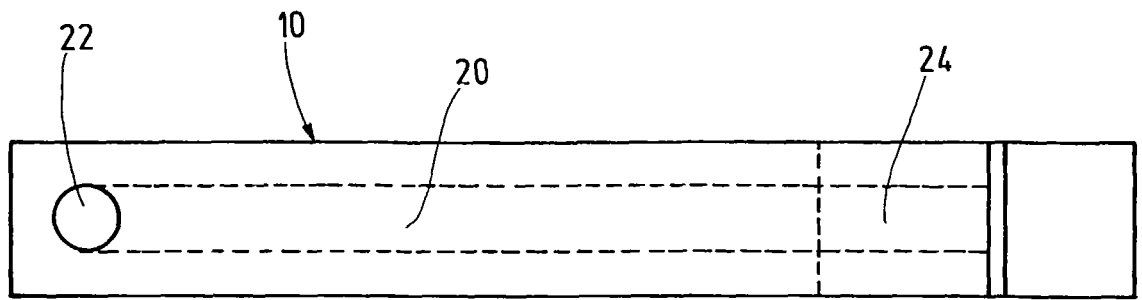
FIGS. 7 and 8 show other embodiments of test strips for the optical analysis of sample liquids each in a top-view and in a central longitudinal section.
Figure 7:
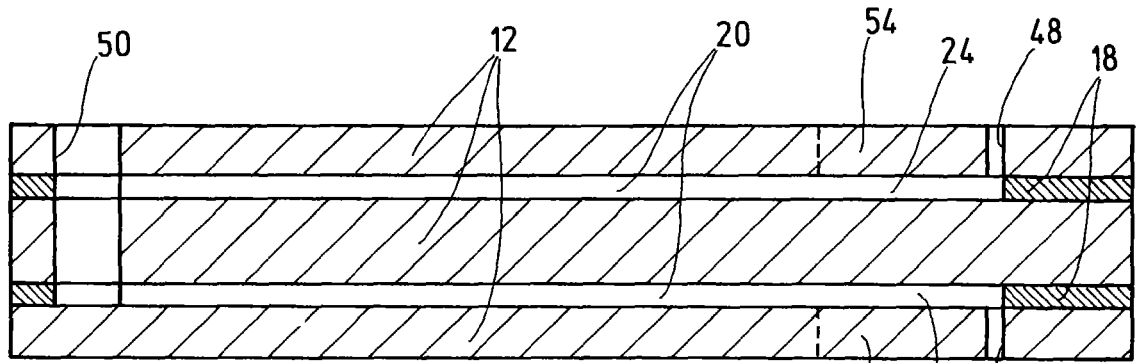
Figure 8:
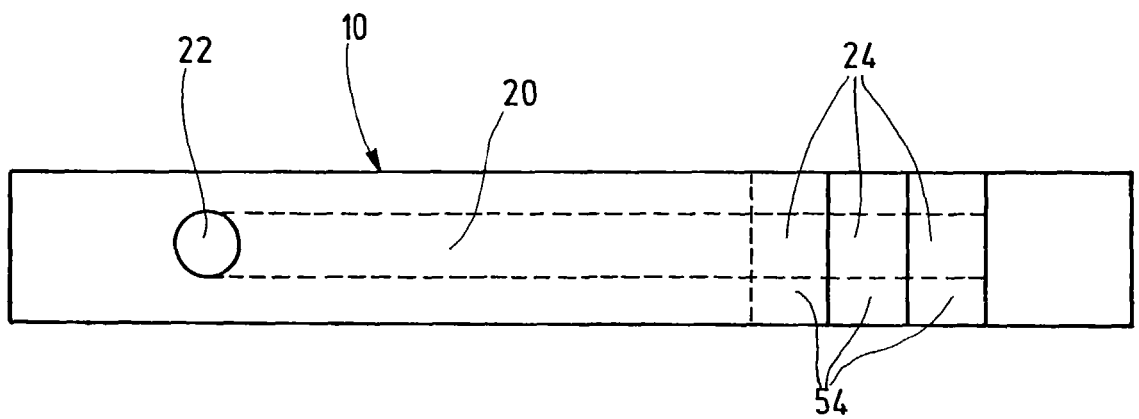
Figure 8:
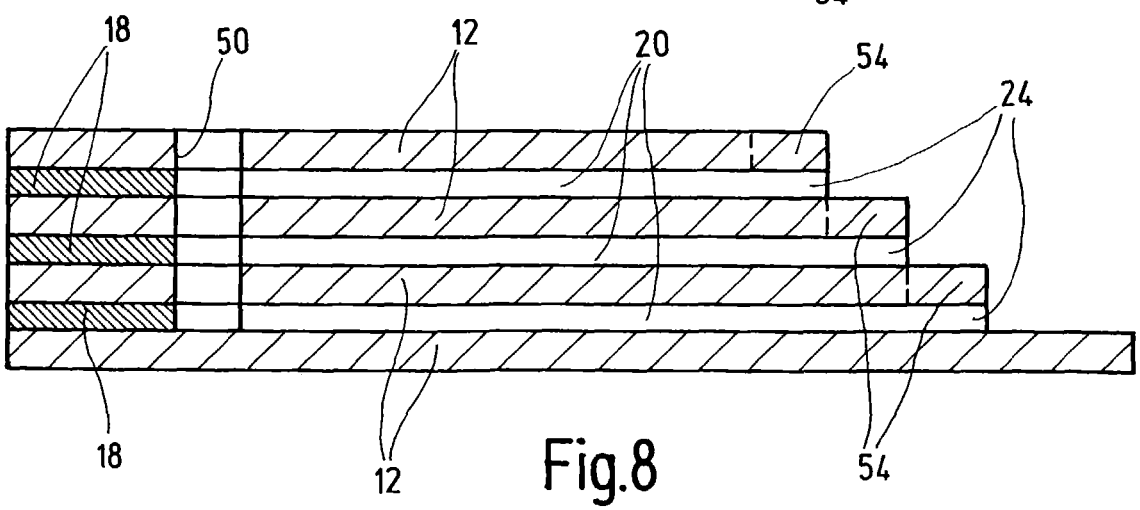

The embodiments of FIGS. 7 and 8 show test strips 10 for the optical and in particular reflection-photometric analysis of a sample liquid. For this purpose the support layers 12 consist of a transparent foil material at least in the area of the measuring windows 54 at the measuring sites 24. Detection reagents that can be taken up by the sample liquid are optionally provided in this area. In the embodiment of FIG. 7 the measuring windows 54 face both sides of the strip whereas they are arranged exposed in a stepped shape on one side of the strip in the embodiment of FIG. 8. Hence in this case several sample channels 20 and associated measuring sites 54 are stacked in a test strip 10 in order to detect a plurality of analytes or enable an additional function check. The test strips can be measured or evaluated amperometrically or optically in an analyser in a known manner.

A field of application for the described test strips 10 is the analysis of blood samples with integrated controls. The target parameter from the blood sample is detected in one of the sample channels. A special control reagent which for example contains a predefined amount of the analyte to be measured is introduced in another sample channel. This analyte is incorporated as a dried reagent film in a third channel in a concentration that is considerably different therefrom. In this manner two measured values are obtained from the same test strip whose concentration difference is known. This ensures that the test strips still function correctly and it is possible to carry out an automatic calibration. Specific properties of the blood sample which may influence the measured value independently of the parameter concentration such as the haematocrit content and the sample temperature can be compensated in this manner.

On-board controls can also be achieved in this manner for electrochemical substrate-enzyme sensors for determining blood coagulation parameters by using suitable reagents to create a rapid and a longer clotting time in the divided blood sample in additional control sample channels. Also in this case the calibration can be adapted from the ratio of the control values according to the properties of the blood sample. It is particularly important in this case to ensure the function of the individual test strips.

Another field of application of the test strips according to the invention are multi-parameter tests (panel testing) in which various measuring parameters are determined simultaneously from the same blood sample in several sample channels arranged above one another. For this purpose suitable reagents are provided in each of the various measuring fields.

What is claimed is:

1. A device for analyzing a biological liquid sample comprising:
    a composite body of a plurality of layers of flat materials defining two or more sample channels, the sample channels extending along a longitudinal dimension of the composite body and being configured for transporting the sample liquid from an application site to two or more measuring sites, wherein
    the plurality of layers of flat materials comprise a plurality of transport layers arranged in a stack-like manner between two support layers,
    the transport layers each comprise two sections having opposing edges which comprise side walls of the sample channels,
    the sides of the support layers that face the transport layers are coated with an electrode layer comprising an electrically conductive material, and
    the support layers are laterally displaced relative to one another in a step-like manner, such that the electrode layers comprise a connecting section extending beyond an adjacent transport layer in a lateral dimension, the lateral dimension being generally perpendicular to the longitudinal dimension of the composite body.

2. The device of claim 1 wherein the two or more sample channels are aligned on top of one another in the direction in which the transport layers are stacked.

3. The device of claim 1 wherein the transport layers comprise an electrically insulating foil material.

4. The device of claim 1 wherein the electrode layers that face the transport layers comprise an electrode pair in the area of the measuring sites for the electro-chemical analysis of the sample.

5. The device of claim 1 wherein the electrode layers comprise a noble metal as a measuring electrode and a silver-silverchloride mixture as a counter reference electrode.

6. The device of claim 5 wherein the noble metal is gold, platinum or palladium.

7. The device of claim 1 wherein the transport layers are separated from at least one adjacent electrode layer by an electrically insulating foil mask.

8. The device of claim 7 wherein the foil mask has perforations in the area of the sample channel for forming at least one of the measuring sites.

9. The device of claim 7 wherein the foil mask is hydrophilic.

10. The device of claim 1 wherein reagents that can be taken up by the sample liquid are provided as a dry substance in the area of at least one of the measuring sites.

11. The device of claim 1 wherein the sample channels provide capillary transport of sample liquid between the application site and the measuring sites.

12. The device of claim 1 wherein the application site comprises inlet openings of the sample channels at an edge of the composite body.

13. The device of claim 1 wherein the application site comprises a recess in the composite body in fluid communication with the sample channels.

14. The device of claim 1 further comprising longitudinally spaced venting channels opening to an outer side of the composite body that are in fluid communication with the sample channels.

15. The device of claim 1 further comprising at least one control site for checking the filling of the sample liquid in at least one of the sample channels, the control site comprising at least one electrode configured to measure electrical conductivity at the at least one control site.

16. The device of claim 1 wherein the support layers comprise transparent measuring windows at least in the area of the measuring sites for the optical examination of the sample liquid.

17. The device of claim 1 wherein at least two of the plurality of layers are glued together.

18. A method of analyzing a biological liquid sample comprising determining different parameters of the sample liquid in respective sample channels of a device according to claim 1.

* * * * *